(12) United States Patent
Safadi et al.

(10) Patent No.: US 9,339,469 B2
(45) Date of Patent: May 17, 2016

(54) R(+)-N-METHYL-PROPARGYL-AMINOINDAN

(71) Applicant: Teva Pharmaceutical Industries, Ltd., Petach-Tikva (IL)

(72) Inventors: Muhammad Safadi, Nazareth (IL); Anton Frenkel, Netanya (IL); Michal Keisar, Kfar-Yona (IL); Danit Licht, Givat Shmuel (IL); Eliezer Bahar, Tel Aviv (IL); Ramy Lidor-Hadas, Kfar-Saba (IL); Marina Zholkovsky, Bat-Yam (IL); Rachel Cohen, Hadera (IL)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 95 days.

(21) Appl. No.: 13/647,622

(22) Filed: Oct. 9, 2012

(65) Prior Publication Data

US 2013/0089610 A1   Apr. 11, 2013

Related U.S. Application Data

(60) Provisional application No. 61/545,426, filed on Oct. 10, 2011.

(51) Int. Cl.
*A61K 9/20* (2006.01)
*A61K 31/135* (2006.01)
*A61K 9/28* (2006.01)

(52) U.S. Cl.
CPC ............ *A61K 9/2013* (2013.01); *A61K 9/2018* (2013.01); *A61K 9/2059* (2013.01); *A61K 9/2846* (2013.01); *A61K 9/2866* (2013.01); *A61K 9/2886* (2013.01); *A61K 31/135* (2013.01)

(58) Field of Classification Search
None
See application file for complete search history.

(56) References Cited

U.S. PATENT DOCUMENTS

| | | | |
|---|---|---|---|
| 5,387,612 A | 2/1995 | Youdim et al. | |
| 5,453,446 A | 9/1995 | Youdim et al. | |
| 5,457,133 A | 10/1995 | Youdim et al. | |
| 5,486,541 A | 1/1996 | Sterling et al. | |
| 5,519,061 A | 5/1996 | Youdim et al. | |
| 5,532,415 A | 7/1996 | Youdim et al. | |
| 5,576,353 A | 11/1996 | Youdim et al. | |
| 5,599,991 A | 2/1997 | Youdim et al. | |
| 5,668,181 A | 9/1997 | Youdim et al. | |
| 5,744,500 A | 4/1998 | Youdim et al. | |
| 5,786,390 A | 7/1998 | Youdim et al. | |
| 5,891,923 A | 4/1999 | Youdim et al. | |
| 6,126,968 A | 10/2000 | Peskin et al. | |
| 6,277,886 B1 | 8/2001 | Levy et al. | |
| 6,316,504 B1 | 11/2001 | Youdim et al. | |
| 6,462,222 B1 | 10/2002 | Chorev et al. | |
| 6,630,514 B2 | 10/2003 | Youdim et al. | |
| 6,956,060 B2 | 10/2005 | Youdim et al. | |
| 7,396,860 B2 | 7/2008 | Blaugrund et al. | |
| 7,491,847 B2 | 2/2009 | Frenkel | |
| 7,547,806 B2 | 6/2009 | Frenkel et al. | |
| 7,572,834 B1 | 8/2009 | Sterling et al. | |
| 7,598,420 B1 | 10/2009 | Sterling et al. | |
| 7,619,117 B1 | 11/2009 | Lidor-Hadas et al. | |
| 7,750,051 B2 | 7/2010 | Frenkel et al. | |
| 7,815,942 B2 | 10/2010 | Peskin | |
| 7,855,233 B2 | 12/2010 | Frenkel et al. | |
| 7,968,749 B2 | 6/2011 | Frenkel et al. | |
| 8,080,584 B2 | 12/2011 | Safadi et al. | |
| 8,143,315 B2 | 3/2012 | Stahl et al. | |
| 8,334,409 B2 | 12/2012 | Frenkel | |
| 8,614,252 B2 | 12/2013 | Frenkel et al. | |
| 8,691,872 B2 | 4/2014 | Lorimer et al. | |
| 2004/0127577 A1 | 7/2004 | Blaugrund et al. | |
| 2006/0018957 A1 | 1/2006 | Lerner et al. | |
| 2006/0094783 A1* | 5/2006 | Youdim et al. | ............. 514/554 |
| 2007/0100001 A1 | 5/2007 | Youdim et al. | |
| 2007/0232700 A1 | 10/2007 | Blaugrund et al. | |
| 2009/0062400 A1 | 3/2009 | Oron et al. | |
| 2009/0076160 A1 | 3/2009 | Lendvai et al. | |
| 2009/0111892 A1 | 4/2009 | Patashnik et al. | |
| 2009/0181086 A1 | 7/2009 | Safadi et al. | |
| 2009/0312436 A1 | 12/2009 | Levy et al. | |
| 2010/0008983 A1 | 1/2010 | Safadi et al. | |
| 2010/0137447 A1 | 6/2010 | Lehmann et al. | |
| 2010/0144887 A1 | 6/2010 | Frenkel et al. | |
| 2010/0145101 A1 | 6/2010 | Frenkel et al. | |
| 2010/0168239 A1 | 7/2010 | Poewe | |
| 2010/0189787 A1* | 7/2010 | Safadi et al. | ............. 424/474 |
| 2010/0189788 A1 | 7/2010 | Safadi et al. | |
| 2010/0189790 A1 | 7/2010 | Safadi et al. | |

(Continued)

FOREIGN PATENT DOCUMENTS

WO   WO 2010/070090   6/2010
WO   WO 2011/003938   1/2011

OTHER PUBLICATIONS

U.S. Appl. No. 12/283,107, filed Sep. 8, 2008, Sterling et al.
U.S. Appl. No. 13/859,625, filed Apr. 9, 2013, Levy et al.
Dec. 6, 2012 International Search Report of the International Searching Authority for International Application No. PCT/US12/59358.
Dec. 6, 2012 Written Opinion of the International Searching Authority for International Application No. PCT/US12/59358.
U.S. Appl. No. 14/092,526, filed Nov. 27, 2013, Levy et al.
U.S. Appl. No. 14/139,212, filed Dec. 23, 2013, Safadi et al.

(Continued)

*Primary Examiner* — Snigdha Maewall
(74) *Attorney, Agent, or Firm* — John P. White; Gary J. Gershik; Cooper & Dunham LLP

(57) ABSTRACT

The subject invention provides R(+)-N-methyl-propargyl-aminoindan or a pharmaceutically acceptable salt thereof and a composition containing R(+)-N-propargyl-1(R)-aminoindan or a pharmaceutically acceptable salt thereof, and a compound of R(+)-N-methyl-propargyl-aminoindan or a salt thereof.

21 Claims, No Drawings

(56) References Cited

U.S. PATENT DOCUMENTS

| | | |
|---|---|---|
| 2010/0189791 A1 | 7/2010 | Safadi et al. |
| 2011/0130466 A1 | 6/2011 | Lorenzl |
| 2011/0152381 A1 | 6/2011 | Frenkel et al. |
| 2011/0313050 A1 | 12/2011 | Rimkus et al. |
| 2012/0003310 A1 | 1/2012 | Safadi et al. |
| 2012/0029087 A1 | 2/2012 | Petit et al. |
| 2012/0059058 A1 | 3/2012 | Lorimer et al. |
| 2012/0100189 A1 | 4/2012 | Safadi et al. |
| 2012/0101168 A1 | 4/2012 | Bahar et al. |
| 2012/0238636 A1 | 9/2012 | Patashnik et al. |
| 2012/0263789 A1 | 10/2012 | Safadi et al. |
| 2013/0089611 A1 | 4/2013 | Ulanenko et al. |
| 2013/0089612 A1 | 4/2013 | Safadi et al. |
| 2013/0345310 A1 | 12/2013 | Rimkus et al. |
| 2014/0051767 A1 | 2/2014 | Fitzer-Attas et al. |
| 2014/0072526 A1 | 3/2014 | Lehmann et al. |
| 2014/0186514 A1 | 7/2014 | Safadi et al. |

OTHER PUBLICATIONS

U.S. Appl. No. 14/310,321, filed Jun. 20, 2014, Bahar et al.

U.S. Appl. No. 14/458,410, filed Aug. 13, 2014, Patashnik et al.

U.S. Appl. No. 14/459,877, filed Aug. 14, 2014, Anton Frenkel and Tamas Koltai.

U.S. Appl. No. 14/524,993, filed Oct. 27, 2017, Erland Blaugrund and Ruth Levy.

U.S. Appl. No. 14/522,456, filed Oct. 23, 2014, Frenkel et al.

International Preliminary Report on Patentability issued Apr. 15, 2014 in connection with International Application No. PCT/US12/59358.

Oct. 2, 2014 Office Action issued by the United States Patent and Trademark Office in connection with U.S. Appl. No. 13/647,658, filed Oct. 9, 2012.

Nov. 13, 2014 Response to Oct. 2, 2014 Office Action issued by the United States Patent and Trademark Office in connection with U.S. Appl. No. 13/647,658, filed Oct. 9, 2013.

Nov. 25, 2014 Office Action issued by the United States Patent and Trademark Office in connection with U.S. Appl. No. 13/647,658, filed Oct. 9, 2014.

Oct. 3, 2013 Office Action issued by the United States Patent and Trademark Office in connection with U.S. Appl. No. 13/647,685, filed Oct. 9, 2012.

Nov. 1, 2014 Response to Oct. 3, 2013 Office Action issued by the United States Patent and Trademark Office in connection with U.S. Appl. No. 13/647,685, filed Oct. 9, 2012.

May 6, 2014 Office Action issued by the United States Patent and Trademark Office in connection with U.S. Appl. No. 13/647,685, filed Oct. 9, 2012.

Aug. 14, 2014 Response to May 6, 2014 Office Action issued by the United States Patent and Trademark Office in connection with U.S. Appl. No. 13/647,685, filed Oct. 9, 2012.

Jan. 5, 2015 Office Action issued by the United States Patent and Trademark Office in connection with U.S. Appl. No. 13/647,685, filed Oct. 9, 2012.

Feb. 24, 2015 Response to Nov. 25, 2014 Office Action issued by the United States Patent and Trademark Office in connection with U.S. Appl. No. 13/647,658, filed Oct. 9, 2014.

* cited by examiner

R(+)-N-METHYL-PROPARGYL-AMINOINDAN

This application claims benefit of U.S. Provisional Application No. 61/545,426, filed Oct. 10, 2011, the entire content of which is hereby incorporated by reference herein.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

U.S. Pat. Nos. 5,532,415, 5,387,612, 5,453,446, 5,457,133, 5,599,991, 5,744,500, 5,891,923, 5,668,181, 5,576,353, 5,519,061, 5,786,390, 6,316,504, 6,630,514, 7,750,051, and 7,855,233 disclose R(+)-N-propargyl-1-aminoindan ("R-PAI"), also known as rasagiline, and its pharmaceutically acceptable salts. These U.S. patents also disclose that rasagiline is a selective inhibitor of the B-form of the enzyme monoamine oxidase ("MAO-B") and is useful in treating Parkinson's disease and various other conditions by inhibition of MAO-B in the brain.

U.S. Pat. Nos. 6,126,968, 7,572,834, and 7,598,420, U.S. patent application Ser. Nos. 12/283,022, and 12/283,107 and PCT publications WO 95/11016 and WO 2006/014973, hereby incorporated by reference, disclose pharmaceutical compositions comprising rasagiline and processes for their preparation.

AZILECT® is a commercially available rasagiline mesylate immediate release formulation indicated for the treatment of the signs and symptoms of idiopathic Parkinson's disease as initial monotherapy and as adjunct therapy to levodopa. The current marketed formulation of rasagiline (Azilect®) is rapidly absorbed, reaching peak plasma concentration ($t_{max}$) in approximately 1 hour. The absolute bioavailability of rasagiline is about 36%. (AZILECT® Product Label, May 2006).

SUMMARY OF THE INVENTION

The subject invention provides a pharmaceutical composition comprising rasagiline or a pharmaceutically acceptable salt thereof, citric acid, R(+)-N-methyl-propargyl-aminoindan or a salt thereof, and at least one pharmaceutically acceptable carrier, wherein R(+)-N-methyl-propargyl-aminoindan is present in the composition in an amount greater than about 0.03%, by weight, relative to the amount of rasagiline, based on a determination HPLC method.

The subject invention also provides a pharmaceutical composition described herein in tablet form.

The subject invention further provides a process for preparing a pharmaceutical composition comprising rasagiline or a pharmaceutically acceptable salt thereof, and at least one pharmaceutically acceptable carrier, comprising:
 a) obtaining a batch of rasagiline or a pharmaceutically acceptable salt thereof;
 b) analyzing the batch for the presence of R(+)-N-methyl-propargyl-aminoindan by a suitable apparatus; and
 c) preparing the pharmaceutical composition from the batch only if the amount of R(+)-N-methyl-propargyl-aminoindan is not more than about 1.0% by weight relative to the amount of rasagiline.

The subject invention yet further provides a process for preparing a packaged pharmaceutical composition comprising rasagiline or a pharmaceutically acceptable salt thereof comprising:
 a) obtaining a pharmaceutical composition of rasagiline or a pharmaceutically acceptable salt thereof;
 b) analyzing the pharmaceutical composition for the presence of R(+)-N-methyl-propargyl-aminoindan by a suitable apparatus; and
 c) packaging the pharmaceutical composition only if the amount of R(+)-N-methyl-propargyl-aminoindan is not more than about 1.0% by weight relative to the amount of rasagiline.

The subject invention yet further ides a process of distributing a validated batch of a pharmaceutical composition comprising rasagiline or a pharmaceutically acceptable salt thereof and at least one pharmaceutically acceptable carrier, comprising:
 a) obtaining a batch of the pharmaceutical position;
 b) performing stability testing with a sample of the batch;
 c) determining the total amount of R(+)-N-methyl-propargyl-aminoindan in the sample of the batch by a suitable apparatus after stability testing;
 d) validating the batch for distribution only if the sample of the batch after stability testing is determined to have not more than about 1.0% by weight of R(+)-N-methyl-propargyl-aminoindan relative to the amount of rasagiline; and
 e) distributing the validated batch.

The subject invention yet further provides R(+)-N-methyl-propargyl-aminoindan or a salt thereof for use, as a reference standard to detect trace amounts of R(+)-N-methyl-propargyl-aminoindan in a pharmaceutical composition comprising rasagiline or a pharmaceutically acceptable salt of rasagiline.

The subject invention yet further provides a method for treating Parkinson's disease in a patient comprising administering to the patient an amount of the pharmaceutical compositions described herein effective to treat Parkinson's disease in the patient.

DETAILED DESCRIPTION OF THE INVENTION

R(+)-N-propargyl-1-aminoindan ("R-PAI"), also known as rasagiline, is a small molecule having the following chemical structure:

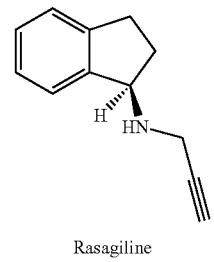

Rasagiline

Rasagiline has been reported to be a selective inhibitor of the B-form of the enzyme monoamine oxidase ("MAO-B") and is useful in treating Parkinson's disease and various other conditions by inhibition of MAO-B in the brain.

A pharmaceutically acceptable salt of rasagiline, rasagiline citrate, and the process of preparing the same has been described in U.S. Pat. No. 7,855,233, the entire content of which is hereby incorporated by reference.

Crystalline rasagiline, and the process of preparing the same has been described in U.S. Pat. Nos. 7,750,051, 7,968,749, the entire contents of which are hereby incorporated by reference.

Delayed release rasagiline formulations have been described in United States Application Publication Nos. 2009/0181086, 2010/0189790, 2010/0189788, 2010/0189787, and 2010/0189791, the entire content of each of which is hereby incorporated by reference.

It has been found that when rasagiline drug substance or drug product is exposed to certain accelerated conditions, an impurity is formed. This impurity was identified to be R(+)-N-methyl-propargyl-aminoindan, having the following structure:

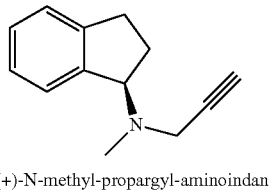

R(+)-N-methyl-propargyl-aminoindan

Other impurities in rasagiline formulations should be avoided, such as rasagiline citramide and R(+)-N-formyl-propargyl-aminoindan.

The subject invention provides a pharmaceutical composition comprising rasagiline or a pharmaceutically acceptable salt thereof, citric acid, R(+)-N-methyl-propargyl-aminoindan or a salt thereof, and at least one pharmaceutically acceptable carrier, wherein R(+)-N-methyl-propargyl-aminoindan is present in the composition in an amount greater than about 0.03%, by weight, relative to the amount of rasagiline, based on a determination by an HPLC method.

In an embodiment of the pharmaceutical composition, the amount of R(+)-N-methyl-propargyl-aminoindan is greater than about 0.1%, by weight, relative to the amount of rasagiline, based on a determination by an HPLC method.

In another embodiment of the pharmaceutical composition, the R(+)-N-methyl-propargyl-aminoindan is present in the pharmaceutical composition in an amount not more than about 1.0%, by weight, relative to the amount of rasagiline, based on a determination by an HPLC method.

In yet another embodiment of the pharmaceutical composition, the pharmaceutical composition is less than one week old, and the temperature during the less than one week did not exceed ambient temperature.

In yet another embodiment of the pharmaceutical composition, the pharmaceutical composition comprises rasagiline as free base.

In yet another embodiment of the pharmaceutical composition, the pharmaceutical composition comprises the pharmaceutically acceptable salt of rasagiline, and which salt is rasagiline citrate.

In yet another embodiment of the pharmaceutical composition, the pharmaceutical composition a solid pharmaceutical composition.

In yet another embodiment of the pharmaceutical composition, the pharmaceutical composition is in tablet form.

In an embodiment of the pharmaceutical composition in tablet form, the tablet has a core and a coating, wherein the core of the tablet comprises an amount of rasagiline as free base, citric acid and mannitol.

In another embodiment of the pharmaceutical composition in tablet form, in the core of the tablet the weight ratio of mannitol to citric acid is between 45 to 1 and 10 to 1.

In yet another embodiment of the pharmaceutical composition in tablet form, in the core of the tablet the weight ratio of mannitol to citric acid is between 30 to 1 and 25 to 1.

In yet another embodiment of the pharmaceutical composition in tablet form, the tablet has a core and a coating, wherein the core of the tablet comprises an amount of rasagiline and citric acid, about 59.9% of mannitol, about 0.53% of aerosil, about 6.6% of starch NF, about 26.3% of pregelatinized starch, about 2.0% of stearic acid, and about 2.0% of talc, by weight, relative to the weight of the core of the tablet.

In yet another embodiment of the pharmaceutical composition in tablet form, the tablet comprises an amount of rasagiline and citric acid, 45.5 mg of mannitol, 0.4 mg of aerosil, 5.0 mg of starch NF, 20.0 mg of pregelatinized starch, 1.5 mg of stearic acid, 1.5 mg of talc, and the coating of the tablet comprises two coating Layers, of which the inner of the two coating layers comprises 3.5 mg of hypromellose and the outer of the two coating layers comprises 4.0 mg of methacrylic acid ethyl acrylate copolymer, 0.8 mg of triethyl citrate, and 1.9 mg of talc extra fine.

In yet another embodiment of the pharmaceutical composition in tablet form, the amount of rasagiline in the core is 0.5 mg.

In yet another embodiment of the pharmaceutical composition in tablet form, the tablet has a core and a coating, wherein the core of the tablet comprises an amount of rasagiline and citric acid, about 59.2% of mannitol, about 0.53% of aerosil, about 6.6% of starch NF, about 26.3% of pregelatinized starch, about 2.0% of stearic acid, and about 2.0% of talc, by weight, relative to the weight of the core of the tablet.

In yet another embodiment of the pharmaceutical composition in tablet form, the core of the tablet comprises an amount of rasagiline and citric acid, 45.0 mg of mannitol, 0.4 mg of aerosil, 5.0 mg of starch NF, 20.0 mg of pregelatinized starch, 1.5 mg of stearic acid, 1.5 mg of talc, and the coating of the tablet comprises two coating layers, of which the inner of the two coating layers comprises 3.5 mg of hypromellose and the outer of the two coating layers comprises 4.0 mg of methacrylic acid ethyl acrylate copolymer, 0.8 mg of triethyl citrate, and 1.9 mg of talc extra fine.

In yet another embodiment of the pharmaceutical composition in tablet form, the amount of rasagiline in the core is 1.0 mg.

In yet another embodiment of the pharmaceutical, not more than 1.0% by weight of rasagiline citramide or a salt thereof is in the pharmaceutical composition relative to the amount of rasagiline.

In yet another embodiment of the pharmaceutical composition, not more than about 1.0% by weight of R(+)-N-formyl-propargyl-aminoindan or a salt thereof is in the pharmaceutical composition relative to the amount of rasagiline.

In yet another embodiment of the pharmaceutical composition, not more than about 0.5% by weight of R(+)-N-formyl-propargyl-aminoindan or a salt thereof is in the pharmaceutical composition relative to the amount of rasagiline.

The subject invention further provides a process for preparing a pharmaceutical composition comprising rasagiline or a pharmaceutically acceptable salt thereof, and at Least one pharmaceutically acceptable carrier, comprising:

a) obtaining a batch of rasagiline or a pharmaceutically acceptable salt thereof;

b) analyzing the batch for the presence of R(+)-N-methyl-propargyl-aminoindan by a suitable apparatus; and c) preparing the pharmaceutical composition from the batch only if the amount of R(+)-N-methyl-propargyl-aminoindan is not more than about 1.0% by weight relative to the amount of rasagiline.

The subject invention yet further provides a process for preparing a packaged pharmaceutical composition comprising rasagiline or a pharmaceutically acceptable salt thereof comprising:

a) obtaining a pharmaceutical composition of rasagiline or a pharmaceutically acceptable salt thereof;

b) analyzing the pharmaceutical composition for the presence of R(+)-N-methyl-propargyl-aminoindan by a suitable apparatus; and c) packaging the pharmaceutical composition only if the amount of R(+)-N-methyl-propargyl-aminoindan is not more than about 1.0% by weight relative to the amount of rasagiline.

The subject invention yet further provides a process of distributing a validated batch of a pharmaceutical composition comprising rasagiline or a pharmaceutically acceptable salt thereof and at least one pharmaceutically acceptable carrier, comprising:

a) obtaining a batch of the pharmaceutical composition;

b) performing stability testing with a sample of the batch;

c) determining the total amount of R(+)-N-methyl-propargyl-aminoindan in the sample of the batch by a suitable apparatus after stability testing;

d) validating the batch for distribution only if the sample of the batch after stability testing is determined to have not more than about 1.0% by weight of R(+)-N-methyl-propargyl-aminoindan relative to the amount of rasagiline; and e) distributing the validated batch.

In an embodiment of any of the processes disclosed herein, the pharmaceutical composition comprises rasagiline free base.

In an embodiment of any of the processes disclosed herein, the pharmaceutical composition comprises rasagiline citrate.

The subject invention yet further provides the use of R(+)-N-methyl-propargyl-aminoindan or a salt thereof, as a reference standard to detect trace amounts of R(+)-N-methyl-propargyl-aminoindan in a pharmaceutical composition comprising rasagiline or a pharmaceutically acceptable salt of rasagiline.

The subject invention yet further provides a method for treating Parkinson's disease in a patient comprising administering to the patient an amount of the pharmaceutical compositions disclosed herein effective to treat Parkinson's disease in the patient.

Every embodiment disclosed herein can be combined with every other embodiment of the subject invention, unless specified otherwise.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2 . . . 49 mg unit amounts are included as embodiments of this invention.

It will be noted that the structure of the compounds this invention includes an asymmetric carbon atom and thus the compounds occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

A characteristic of a compound refers to any quality that a compound exhibits, e.g., peaks or retention times, as determined by 1H nuclear magnetic spectroscopy, mass spectroscopy, infrared, ultraviolet or fluorescence spectrophotometry, gas chromatography, thin layer chromatography, high performance liquid chromatography (HPLC), elemental analysis, Ames test, dissolution, stability and any other quality that can be determined by an analytical method. Once the characteristics of a compound are known, the information can be used to, for example, screen or test for the presence of the compound in a sample. Quantity or weight percentage of a compound present in a sample can be determined by a suitable apparatus, for example, a HPLC.

As used herein, a "pharmaceutically acceptable salt" of rasagiline includes citrate, tannate, malate, mesylate, maleate, fumarate, tartrate, esylate, p-toluenesulfonate, benzoate, acetate, phosphate and sulfate salts. For the preparation of pharmaceutically acceptable acid addition salts of the compounds of the invention, the free base can be reacted with the desired acids in the presence of a suitable solvent by conventional methods.

Rasagiline can also be used in its free base form. A process of manufacture of the rasagiline free base is described in U.S. Pat. Nos. 7,750,051 and 7,968,749, the contents of which are hereby incorporated by reference.

As used herein, "drug substance" refers to the active ingredient in a drug product, which provides pharmacological activity or other direct effect in the diagnosis, cure, mitigation, treatment, or prevention of disease, or to affect the structure or any function of the body of man or animals.

As used herein, "drug product" refers to the finished dosage form containing the drug substance as well as at least one pharmaceutically acceptable carrier.

As used herein, an "isolated" compound is a compound isolated from the crude reaction mixture following an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided following an affirmative act intended to purify the composition by separating the chemical entity from the composition.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life. For example, detailed requirements of stability testing for finished pharmaceuticals are codified in 21 C.F.R §211.166, the entire content of which is hereby incorporated by reference.

As used herein, a pharmaceutical composition which is "X weeks old" refers to the period of time, in this case one week, since the pharmaceutical composition was made.

As used herein, "ambient temperature" refers a temperature of from about 20° C. to about 30° C.

A "detection limit" for an analytical method used in screening or testing for the presence of a compound in a sample is a threshold under which the compound in a sample cannot be detected by the analytical method, e.g. an HPLC, MS, NMR, or FT-IR method.

As used herein, "about" in the context of a measurable numerical value means the numerical value within the standard error of the analytical method used to measure.

A dosage unit may comprise a single compound or mixtures of compounds thereof. A dosage unit can be prepared for oral dosage forms, such as tablets, capsules, pills, powders, and granules.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

Specific examples of pharmaceutical acceptable carriers and excipients that may be used to formulate oral dosage forms are described, e.g., in U.S. Pat. No. 6,126,968 to Peskin et al., issued Oct. 3, 2000. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, melting agents, stabilizing agents, solubilizing agents, antioxidants, buffering agent, chelating agents, fillers and plasticizers. For instance, for oral administration in the dosage unit form of a tablet or capsule, the active drug component can be combined with an oral, non-toxic, pharmaceutically acceptable, inert carrier such as gelatin, agar, starch, methyl cellulose, dicalcium phosphate, calcium sulfate, mannitol, sorbitol and the like. Suitable binders include starch, gelatin, natural sugars such as corn starch, natural and synthetic gums such as acacia, tragacanth, or sodium alginate, povidone, carboxymethylcellulose, polyethylene glycol, waxes, and the like. Antioxidants include ascorbic acid, fumaric acid, citric acid, malic acid, gallic acid and its salts and esters, butylated hydroxyanisole, editic acid. Lubricants used in these dosage forms include sodium oleate, sodium stearate, sodium benzoate, sodium acetate, stearic acid, sodium stearyl fumarate, talc and the like. Disintegrators include, without limitation, starch, methyl cellulose, agar, bentonite, xanthan gum, croscarmellose sodium, sodium starch glycolate and the like, suitable plasticizers include triacetin, triethyl citrate, dibutyl sebacate, polyethylene glycol and the like.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Stability Study of Rasagiline Base Drug Substance

Rasagiline base drum substance was subject to stability testing under various storage conditions. Rasagiline base drug substance was prepared according to procedures described in Examples 1-3 of U.S. Pat. No. 7,968,749.

The observed melting point of Rasagiline base is 38-41° C. so it appears as a liquid melt at elevated temperatures. This is the reason for performing the degradation study of rasagiline base at 78° C.-90° C. in melt phase.

Samples of Rasagiline base were introduced into amber glass vials, closed with stoppers and covered with aluminium foil for protection from light. Samples intended to degrade under en inert atmosphere were flushed with nitrogen for 5 minutes before closing with a stepper.

The samples were introduced into a pre-heated oven and held at a constant temperature of 78 and 90° C. for 24, 72 or 137 hrs. After completion of the treatment the samples were refrigerated and analyzed. The results are summarized in Table 1 below which shows that no R(+)-N-methyl-PAI was formed.

TABLE 1

Rasagiline base degradation in melt phase

| Exp. No. | Atm. | Temp. deg. C. | Time hrs | R(+)-N-methyl-PAI, % of Rasagiline |
|---|---|---|---|---|
| 1 | $N_2$ | 78 | 24 | N.A. |
| 2 | $N_2$ | 78 | 72 | N.A. |
| 3 | Air | 78 | 24 | N.A. |
| 4 | Air | 78 | 72 | N.A. |
| 5 | Air | 90 | 24 | N.D. |
| 6 | Air | 90 | 72 | N.D. |
| 7 | Air | 90 | 137 | N.D. |

N.D.—not detected
N.A.—not available

R(+)-N-methyl-PAI was monitored in the drug products during the stability study and was found in the validation batches after 6 months storage at accelerated conditions (40° C./75% RH) at the 0.1% the Quantitation Level) for the 0.5 mg formulation and at levels of up to 0.3% for the 1 mg formulation. It was not seen in any batch after 12 months under real-time storage conditions (25° C./60% RH).

Example 2

Preparation of R(+)-methyl-propargyl-aminoindan

R(+)-N-methyl-PAI HCl can be synthesized by methylation of R(+)-PAI and can be isolated as crystalline hydrochloride salt.

For example, a method for preparing hydrochloride salt of R(+)-N-methyl-PAI has been described in U.S. Pat. No. 5,744,500, the entire content of which is incorporated by reference.

As described in U.S. Pat. No. 5,744,500, 1.2 g of R(+)-PAI free base, 0.97 g of potassium carbonate and 1 g of methyl iodide were added to 15 ml of acetone and the resulting suspension was heated to reflux under a nitrogen atmosphere for 8 hours. The volatiles were then removed under reduced pressure and the residue partitioned between 10% aqueous sodium hydroxide (30 ml) and methylene chloride (30 ml). The organic phase was dried by removing the solvent in vacuo. The residue was flash chromatographed on silica gel eluting with 40% ethyl acetate/60% hexane. Fractions containing R(+)-N-methyl-PAI free base were combined and the solvent was replaced by diethyl ether. The ethereal solution was then treated with gaseous HCl and the colaties were removed in vacuo. The residue recrystallized from isopropanol to yield 400 mg of R(+)-N-methyl-PAI HCl as a white crystalline solid, m.p. 134-136° C., $[\alpha]_D$+31.40 (ethanol). NMR δ (CDCl$_3$): 2.55 (2H,m); 2.7 (1H,br.s); 2.8 (3H,s); 3.0 (1H,m); 3.4 (1H,m); 3.9 (2H,br.s); 5.05 (1H,m); 7.7 (4H,m) ppm.

R(+)-N-methyl-PAI HCl was characterized by elemental analysis, HPLC, $^1$H-NMR, $^{13}$C-NMR, ATR and MS.

Elemental Analysis

The analysis for C, H and N was performed using a Perkin-Elmer 2400 series II analyzer. Analysis for Cl was performed using the oxygen-flask combustion method (Schoniger application) and subsequent potentiometric titration by the 835 Titrando Metrohm Tiroprocessor.

Element Analysis Results for R(+)-N-Methyl-PAI HCl

| Element | % C | % H | % N | % Cl |
|---|---|---|---|---|
| Theoretical | 70.42 | 7.27 | 6.32 | 15.99 |
| Experimental | 70.27 | 7.20 | 6.29 | 16.38 |

The results of the elemental analysis correspond to the molecular formula.

HPLC Chromatogram

The prepared R(+)-N-methyl-PAI elutes at good chromatographic purity (99.67% area in a HPLC chromatogram).

NMR Spectroscopy

The $^1$H-NMR and $^{13}$C-NMR spectra of R(+)-N-methyl-PAI hydrochloride were recorded on a Bruker 300 MHz NMR instrument at 300.1 and 75.5 MHz respectively. The spectra were run at room temperature (T=300K) in DMSO-D$_6$ as a solvent with TMS as internal reference. The shift assignments are summarized in Table 2. The spectra are fully consistent with the expected structure.

Structure of R(+)-N-ME-PAI HCL with Designations used for the Attribution of $^1$H-NMR and $^{13}$C-NMR Shifts

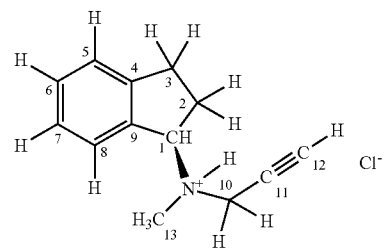

TABLE 2

$^1$H-NMR and $^{13}$C-NMR Chemical Shifts of N—Me-PAI HCl in DMSO-D$_6$ at T = 300 K

| | $^{13}$C (ppm) | $^1$H (ppm) | Multiplicity[1] |
|---|---|---|---|
| C#1 | 67.56 & 68.00 | 1H 5.06, 5.11 | 2 brm |
| C#2 | 24.07 & 24.57 | 2H 2.30-2.60 | brs (with DMSO) |
| C#3 | 30.14 | 1H 2.90 | brm |
| | | 1H 3.14 | brm |
| C#4 | 145.31 & 146.13 | — | — |
| C#5 | 129.74 | 3H 7.25-7.45 | brm |
| C#6 | 125.17 | | |
| C#7 | 126.70 | | |
| C#8 | 127.12 | 1H 81, 7.91 | 2 brm |
| C#9 | 134.58 & 135.46 | — | — |
| C#10 | 40.95 & 42.96 | 2H 4.08 | brm |
| C#11 | 80.99 | — | — |
| C#12 | 73.73 | 1H 2.51, 2.66 | brm (with DMSO) |
| C#13 | 34.14 & 36.62 | 3H 3.41, 3.86 | brs |
| NH | — | 1H 12.08 | brs |

[1]brs = broad singlet;
brm = broad multiplet

ATR Spectrum

The FT-IR (using ATR) spectrum of R(+)-N-methyl-PAI hydrochloride was measured with a Thermo Scientific Nicolet 6700 FT-IR apparatus. The IR spectrum exhibits typical absorption bands of acetylene vibration at 2120 and 3201.

Mass Spectroscopy (MS)

The mass spectrum of R(+)-N-methyl-PAI hydrochloride was performed on AB Applied Biosystems Sciex API 4000 LC/MS/MS system.

The mass spectrum exhibits quasi-molecular ions at m/z 181 [M+H$^+$] and fragmentation ions at 39; 70; 91 and 117. The spectrum is in agreement with the molecular formula of R(+)-N-methyl-PAI.

What is claimed is:

1. A pharmaceutical composition comprising rasagiline or a pharmaceutically acceptable salt thereof, citric acid, R(+)-N-methyl-propargyl-aminoindan or a salt thereof, and at least one pharmaceutically acceptable carrier, wherein R(+)-N-methyl-propargyl-aminoindan is present in the composition in an amount greater than about 0.03%, and not more than about 1.0%, by weight, relative to the amount of rasagiline, based on a determination by an HPLC method.

2. The pharmaceutical composition of claim 1, wherein the amount of R(+)-N-methyl-propargyl-aminoindan is greater than about 0.1%, by weight, relative to the amount of rasagiline, based on a determination by an HPLC method.

3. The pharmaceutical composition of claim 1, wherein the pharmaceutical composition is less than one week old, and the temperature during the less than one week did not exceed ambient temperature.

4. The pharmaceutical composition of claim 1, which comprises rasagiline as free base.

5. The pharmaceutical composition of claim 1, which comprises the pharmaceutically acceptable salt of rasagiline, and which salt is rasagiline citrate.

6. The pharmaceutical composition of claim 1, wherein the pharmaceutical composition is a solid pharmaceutical composition.

7. The pharmaceutical composition of claim 6 which is in tablet form.

8. The pharmaceutical composition of claim 7 having a core and a coating, wherein the core of the tablet comprises an amount of rasagiline free base, citric acid and mannitol.

9. The pharmaceutical composition of claim 8 wherein in the core of the tablet the weight ratio of mannitol to citric acid is between 45 to 1 and 10 to 1.

10. The pharmaceutical composition of claim 9 wherein in the core of the tablet the weight ratio of mannitol to citric acid is between 30 to 1 and 25 to 1.

11. The pharmaceutical composition of claims 7 having a core and a coating, wherein the core of the tablet comprises an amount of rasagiline and citric acid, about 59.9% of mannitol, about 0.53% of aerosil, about 6.6% of starch NF, about 26.3% of pregelatinized starch, about 2.0% of stearic acid, and about 2.0% of talc, by weight, relative to the weight of the core of the tablet.

12. The pharmaceutical composition of claim 11, wherein the core of the tablet comprises an amount of rasagiline and citric acid, 45.5 mg of mannitol, 0.4 mg of aerosil, 5.0 mg of starch NF, 20.0 mg of pregelatinized starch, 1.5 mg of stearic acid, 1.5 mg of talc, and the coating of the tablet comprises two coating layers, of which the inner of the two coating layers comprises 3.5 mg of hypromellose and the outer of the two coating layers comprises 4.0 mg of methacrylic acid ethyl acrylate copolymer, 0.8 mg of triethyl citrate, and 1.9 mg of talc extra fine.

13. The pharmaceutical composition of claim 8, wherein the amount of rasagiline in the core is 0.5 mg.

14. The pharmaceutical composition of claim 7 having a core and a coating, wherein the core of the tablet comprises an amount of rasagiline and citric acid, about 59.2% of mannitol, about 0.53% of aerosil, about 6.6% of starch NF, about 26.3% of pregelatinized starch, about 2.0% of stearic acid, and about 2.0% of talc, by weight, relative to the weight of the core of the tablet.

15. The pharmaceutical composition of claim 14, wherein the core of the tablet comprises an amount of rasagiline and citric acid, 45.0 mg of mannitol, 0.4 mg of aerosil, 5.0 mg of starch NF, 20.0 mg of pregelatinized starch, 1.5 mg of stearic acid, 1.5 mg of talc, and the coating of the tablet comprises two coating layers, of which the inner of the two coating layers comprises 3.5 mg of hypromellose and the outer of the two coating layers comprises 4.0 mg of methacrylic acid ethyl acrylate copolymer, 0.8 mg of triethyl citrate, and 1.9 mg of talc extra fine.

16. The pharmaceutical composition of claim 8, wherein the amount of rasagiline in the core is 1.0 mg.

17. The pharmaceutical composition of claim 1, wherein not more than 1.0% by weight of rasagiline citramide or a salt thereof is present in the pharmaceutical composition relative to the amount of rasagiline.

18. A process for preparing a pharmaceutical composition comprising rasagiline or a pharmaceutically acceptable salt thereof, and at least one pharmaceutically acceptable carrier, comprising:
  a) obtaining a batch of rasagiline or a pharmaceutically acceptable salt thereof;
  b) analyzing the batch for the presence of the compound recited by claim 1 by a suitable apparatus; and
  c) preparing the pharmaceutical composition from the batch only if the amount of the compound is not more than about 1.0% by weight relative to the amount of rasagiline.

19. A process for preparing a packaged pharmaceutical composition comprising rasagiline or a pharmaceutically acceptable salt thereof comprising:
  a) obtaining a pharmaceutical composition of rasagiline or a pharmaceutically acceptable salt thereof;
  b) analyzing the pharmaceutical composition for the presence of the compound recited by claim 1 by a suitable apparatus; and
  c) packaging the pharmaceutical composition only if the amount of the compound is not more than about 1.0% by weight relative to the amount of rasagiline.

20. A process of distributing a validated batch of a pharmaceutical composition comprising rasagiline or a pharmaceutically acceptable salt thereof and at least one pharmaceutically acceptable carrier, comprising:
  a) obtaining a batch of the pharmaceutical composition;
  b) performing stability testing with a sample of the batch;
  c) determining the total amount of the compound recited by claim 1 in the sample of the batch by a suitable apparatus after stability testing;
  d) validating the batch for distribution only if the sample of the batch after stability testing is determined to have not more than about 1.0% by weight of the compound relative to the amount of rasagiline; and
  e) distributing the validated batch.

21. A method for treating Parkinson's disease in a patient comprising administering to the patient an amount of the pharmaceutical composition of claim 1 effective to treat Parkinson's disease in the patient.

* * * * *